US012150942B2

(12) United States Patent
Coffey et al.

(10) Patent No.: US 12,150,942 B2
(45) Date of Patent: Nov. 26, 2024

(54) CERDULATINIB FOR TREATING MYELOMA

(71) Applicant: Alexion Pharmaceuticals, Inc., Boston, MA (US)

(72) Inventors: Gregory Coffey, Emerald Hills, CA (US); Jiajia Feng, Union City, CA (US)

(73) Assignee: Alexion Pharmaceuticals, Inc., Boston, MA (US)

( * ) Notice: Subject to any disclaimer, the term of this patent is extended or adjusted under 35 U.S.C. 154(b) by 206 days.

(21) Appl. No.: 17/092,137

(22) Filed: Nov. 6, 2020

(65) Prior Publication Data

US 2021/0299125 A1 Sep. 30, 2021

Related U.S. Application Data

(63) Continuation of application No. 16/831,471, filed on Mar. 26, 2020, now abandoned, which is a continuation of application No. 15/235,972, filed on Aug. 12, 2016, now abandoned.

(60) Provisional application No. 62/342,711, filed on May 27, 2016, provisional application No. 62/204,400, filed on Aug. 12, 2015.

(51) Int. Cl.
*A61K 31/506* (2006.01)
*A61K 45/06* (2006.01)
*A61P 35/02* (2006.01)

(52) U.S. Cl.
CPC ............ *A61K 31/506* (2013.01); *A61K 45/06* (2013.01); *A61P 35/02* (2018.01)

(58) Field of Classification Search
CPC .... A61K 31/445; A61K 31/4168; A61P 35/00
See application file for complete search history.

(56) References Cited

U.S. PATENT DOCUMENTS

| | | |
|---|---|---|
| 7,449,456 B2 | 11/2008 | Nagashima et al. |
| 7,557,210 B2 | 7/2009 | Singh et al. |
| 8,012,959 B2 | 9/2011 | Nagashima et al. |
| 8,138,339 B2 | 3/2012 | Bauer et al. |
| 8,501,944 B2 | 8/2013 | Bauer et al. |
| 8,937,070 B2 | 1/2015 | Bauer et al. |
| 9,357,229 B2 | 6/2016 | Vannucchi et al. |
| 9,868,729 B2 | 1/2018 | Bauer et al. |
| 2004/0029902 A1 | 2/2004 | Singh et al. |
| 2006/0276459 A1* | 12/2006 | Masuda ............... A61K 31/542 514/224.2 |
| 2009/0318407 A1* | 12/2009 | Bauer ................ A61K 31/5355 544/323 |
| 2011/0294749 A1 | 12/2011 | Nagashima et al. |
| 2012/0129867 A1 | 5/2012 | Bauer et al. |
| 2012/0157500 A1* | 6/2012 | Tao ........................ A61K 45/06 514/345 |
| 2013/0237493 A1* | 9/2013 | Sinha .................... A61K 31/506 514/48 |
| 2014/0031361 A1 | 1/2014 | Bauer et al. |
| 2014/0315911 A1* | 10/2014 | Jin .......................... A61P 35/00 514/249 |
| 2014/0371241 A1 | 12/2014 | Buggy et al. |
| 2015/0094298 A1 | 4/2015 | Bauer et al. |
| 2017/0042896 A1 | 2/2017 | Coffey et al. |
| 2018/0147203 A1 | 5/2018 | Pandey et al. |
| 2018/0353506 A1 | 12/2018 | Coffey et al. |

FOREIGN PATENT DOCUMENTS

| | | |
|---|---|---|
| EP | 1518855 | 3/2005 |
| WO | WO 2008/009458 | 1/2008 |
| WO | WO 2009/145856 | 12/2009 |
| WO | WO 2010/129802 | 11/2010 |
| WO | WO 2012/045020 | 4/2012 |
| WO | WO 2016/040858 | 3/2016 |
| WO | WO 2016/196385 | 12/2016 |
| WO | WO 2017/027829 | 2/2017 |
| WO | WO 2017/096303 | 6/2017 |

OTHER PUBLICATIONS

Coffey, (Journal of Pharmacology and Experimental Therapeutics vol. 351 pp. 538-548). (Year: 2014).*
Li et al, (Neoplasia vol. 12 pp. 28-38. Published 2010). (Year: 2010).*
Burger et al., (Molecular Cancer Therapeutics vol. 8 pp. 26-35. Published 2009). (Year: 2009).*
Scuto et al, (Leukemia vol. 25 pp. 538-550 published 2011). (Year: 2011).*
American Cancer Society: Multiple Myeloma How is it staged?, (Year: 2018).*
Shimura et al (Molecular Cancer Therapeutics vol. 11 pp. 2600-2609 (2011). (Year: 2011).*
Stedman's Medical Dictionary (27th edition pp. 865-866 published 2000). (Year: 2000).*
Bupathi (Blood vol. 118 p. 3832 published 2011) (Year: 2011).*
Reagan-Shaw (FASEBJ vol. 22 pp. 659-661, published 2007) (Year: 2007).*
Blunt et al., "The dual Syk/JAK inhibitor cerdulatinib antagonises B-cell receptor and microenvironmental signaling in chronic lymphocytic leukemia.", Clinical Cancer Research: An Official Journal of the American Association for Cancer Research Oct. 3, 2016, Oct. 3, 2016 (Oct. 3, 2016), XP002767268, ISSN: 1078-0432.
Blunt et al., "The Syk\Jak Inhibitor Cerdulatinib (PRT062070) Shows Promising Preclinical Activity in Chronic Lymphocytic Leukemia by Antagonising B Cell Receptor and Microenvironmental Signalling", Blood, American Society of Hematology, US, vol. 126, No. 23, Dec. 3, 2015 (Dec. 3, 2015), XP009193491, ISSN: 0006-4971.

(Continued)

*Primary Examiner* — Clinton A Brooks
*Assistant Examiner* — George W Kosturko
(74) *Attorney, Agent, or Firm* — Sheppard Mullin Richter & Hampton LLP

(57) ABSTRACT

Compositions and methods for treating multiple myeloma (MM), acute myeloid lymphoma (AML) or a myeloproliferative disease (MPD) in a human patient in need thereof. The methods entail administering to the patient an effective amount of cerdulatinib.

22 Claims, 7 Drawing Sheets

(56) References Cited

OTHER PUBLICATIONS

Burger, et al. Janus kinase inhibitor INCB20 has antiproliferative and apoptotic effects on human myeloma cells in vitro and in vivo. Molecular Cancer Therapeutics. 2009; 8:26-35.
Coffey et al., "The Novel Kinase Inhibitor PRT062070 (Cerdulatinib) Demonstrates Efficacy in Models of Autoimmunity and B-Cell Cancer", The Journal of Pharmacology and Experimental Therapeutics, 2014, vol. 351, No. 3, pp. 538-548.
Hamlin et al., "Clinical and Correlative Results of a Phase 1 Study of Cerdulatinib (PRT062070) a Dual SYK/JAK Inhibitor in Patients with Relapsed/Refractory B Cell Malignancies", Blood, vol. 126, No. 23, Dec. 3, 2015 (Dec. 3, 2015), XP009193500, & 57th Annual Meeting of the American-Society-Of Hematology; Orlando, FL, USA; Dec. 5-8, 2015.
How Is Multiple Myeloma Staged? printed Aug. 17, 2017. https://www.cancer.org/cancer/multiple-myeloma/detection-diagnosisstaging/staging.html.
International Search Report and Written Opinion for PCT/US2016/034861 dated Sep. 7, 2016, 8 pages.
International Search Report and Written Opinion for PCT/US2016/046862 dated Oct. 31, 2016, 9 pages.
International Search Report and Written Opinion for PCT/US2016/064824 dated Jul. 5, 2017, 15 pages.
Li, et al. INCB16562, a JAK1/2 selective inhibitor, is efficacious against multiple myeloma cells and reverses the protective effects of cytokine and stromal cell support. Neoplasia. 2010; 12:28-38.
Ma et al., "Cerdulatinib, a novel dual SYK/JAK kinase inhibitor, has broad anti-tumor activity in both ABC and GCB types of diffuse large B cell lymphoma.", Oncotarget, vol. 6, No. 41, Nov. 5, 2015 (Nov. 5, 2015), pp. 43881-43896, XP002767267, ISSN: 1949-2553.
Patel et al., "A Phase I Open-Label, Multi-Dose Escalation Study of the Dual Syk/Jak Inhibitor PRT062070 (Cerdulatinib) in Patients with Relapsed/Refractory B Cell Malignancies", Blood, vol. 124, No. 21, Dec. 2014 (Dec. 2014), XP009193499, & 56th Annual Meeting of the American-Society-Of-Hematology; San Francisco, CA, USA; Dec. 6-9, 2014.
Reagan-Shaw et al., "Dose translation from animal to human studies revisited", FASEB Journal, 2007, vol. 22, pp. 659-661.
Scuto et al., "The novel JAK inhibitor AZD1480 blocks STAT3 and FGFR3 signaling, resulting in suppression of human myeloma cell growth and survival", Leukemia, 2011, 25(3), pp. 538-550.
Shimura et al., "RSK2ser227 at N-Terminal Kinase Domain Is a Potential Therapeutic Target for Multiple Myeloma", Molecular Cancer Therapeutics, 2012, 11(12), pp. 2600-2609.
Stedman's Medical Dictionary 27th Edition, 2000, pp. 865-866.

* cited by examiner

CERDULATINIB FOR TREATING MYELOMA

CROSS REFERENCE TO RELATED APPLICATIONS

This application is a continuation of U.S. patent application Ser. No. 16/831,471, filed Mar. 26, 2020, which is a continuation of U.S. patent application Ser. No. 15/235,972, filed Aug. 12, 2016, now abandoned, which claims priority to and the benefit under 35 U.S.C. § 119(e) to U.S. Provisional Patent Application Ser. No. 62/204,400, filed on Aug. 12, 2015, and U.S. Provisional Patent Application Ser. No. 62/342,711, filed on May 27, 2016, the entire disclosure of each of which is hereby incorporated by reference.

BACKGROUND

Multiple myeloma (MM) is a cancer of plasma cells, a type of white blood cell normally responsible for producing antibodies. In multiple myeloma, collections of abnormal plasma cells accumulate in the bone marrow, where they interfere with the production of normal blood cells. Most cases of multiple myeloma also feature the production of a paraprotein, an abnormal antibody which can cause kidney problems. Bone lesions and hypercalcemia (high blood calcium levels) are also often encountered.

Multiple myeloma is diagnosed with blood tests (serum protein electrophoresis, serum free kappa/lambda light chain assay), bone marrow examination, urine protein electrophoresis, and X-rays of commonly involved bones. Multiple myeloma is considered to be incurable but treatable. Remission may be induced with steroids, chemotherapy, proteasome inhibitors, immunomodulatory drugs such as thalidomide or lenalidomide, and stem cell transplants. Radiation therapy is sometimes used to reduce pain from bone lesions.

Patients with multiple myeloma have an abnormally large number of identical plasma cells, and they also have too much of one type of antibody. The tumor, its products, and the host response to it result in a number of organ dysfunctions and symptoms of bone pain or fracture, renal failure, susceptibility to infection, anemia, hypercalcemia, and occasionally clotting abnormalities, neurologic symptoms, and vascular manifestations of hyperviscosity.

Multiple myeloma develops in 6.1 per 100,000 people per year. It is more common in men and is twice as common in African Americans as it is in White Americans. With conventional treatment, median survival is 3-4 years, which may be extended to 5-7 years or longer with advanced treatments. Multiple myeloma is the second most common hematological malignancy in the U.S. (after non-Hodgkin lymphoma), and constitutes 1% of all cancers. The five year survival rate is 45%.

Two relatively new classes of anti-cancer agents for multiple myeloma are being developed, thalidomide (including the immunomodulatory derivatives such as lenalidomide) and the proteasome inhibitors including bortezomib. A significant proportion of multiple myeloma patients are resistant to those agents, and initial responders (even those achieving durable complete remissions) can eventually relapse.

Acute myeloid leukemia (AML), also known as acute myelogenous leukemia or acute nonlymphocytic leukemia (ANLL), is a cancer of the myeloid line of blood cells, characterized by the rapid growth of abnormal white blood cells that accumulate in the bone marrow and interfere with the production of normal blood cells. AML is the most common acute leukemia affecting adults, and its incidence increases with age. Although AML is a relatively rare disease, accounting for roughly 1.2% of cancer deaths in the United States, its incidence is expected to increase as the population ages. The myeloproliferative neoplasms (MPNs), or myeloproliferative diseases (MPDs), are a group of diseases of the bone marrow in which excess cells are produced. They are related to, and may evolve into, myelodysplastic syndrome and acute myeloid leukemia.

The development of more efficacious therapies for MM, AML and MPD is urgently needed.

SUMMARY

The present examples demonstrate that cerdulatinib dose-dependently activated apoptosis and inhibit cell proliferation of various multiple myeloma (MM) cell lines. Further, such activity of cerdulatinib is independent of FGFR3. Moreover, the anti-cancer activity of cerdulatinib was also demonstrated in other myeloma cancer cells including those of acute myeloid lymphoma (AML) and myeloproliferative diseases (MPD). Therefore, the experimental data presented here show that cerdulatinib is an efficacious anti-cancer agent for various myelomas and plasma cell disorders.

Cerdulatinib is a small molecule, ATP-competitive, reversible inhibitor of both SYK and JAK family members and is described in U.S. Pat. No. 8,138,339. Cerdulatinib has a chemical name of 4-(cyclopropylamino)-2-(4-(4-(ethylsulfonyl)piperazin-1-yl)phenylamino)pyrimidine-5-carboxamide, and the structure of formula I:

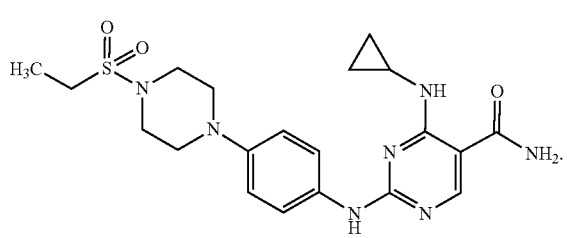

In one embodiment, the present disclosure provides a method of treating multiple myeloma (MM), acute myeloid lymphoma (AML) or a myeloproliferative disease (MPD) in a human patient in need thereof, comprising administering to the patient an effective amount of cerdulatinib or a pharmaceutically acceptable salt thereof. The effective amount can be from about 5 mg to about 150 mg daily.

In some embodiments, the patient is not being treated with fludarabine. In some embodiments, the patient is not being treated with a purine analog. In some embodiments, the patient is not being treated with an agent that interferes with DNA synthesis.

The administration may be once daily or twice daily. When administered twice daily, the effective amount may be from about 25 mg to about 65 mg twice daily, or more specifically about 30 mg, 35 mg, 40 mg, 45 mg, or 50 mg twice daily.

In some embodiments, the patient suffers from an advanced malignancy of MM, AML or MPD. In some embodiments, the patient has relapsed or not responded to a prior chemotherapy. In some embodiments, the patient has failed at least two prior therapies. In some embodiments, the multiple myeloma is a Stage I, Stage II, or Stage III multiple myeloma.

In some embodiments, the patient has an albumin level lower than 3.5 mg/dL. In some embodiments, the patient has a B2-microglobulin level from 3.5 to 5 mg/L or greater than 5 mg/L. In some embodiments, the patient has an FGFR3 activation mutation.

Non-limiting examples of multiple myeloma include Monoclonal Gammopathy of Undetermined Significance (MGUS), Asymptomatic (Smoldering/Indolent) Myeloma, or Symptomatic (Active) Myeloma.

In some embodiments, the method further comprises administering to the patient a second agent, which may be a P90RSK inhibitor or selected from the group consisting of dexamethasone, melphalan, doxorubicin, bortezomib, lenalidomide, prednisone, carmustine, etoposide, cisplatin, vincristine, cyclophosphamide, BI-D1870, and thalidomide.

DETAILED DESCRIPTION

Figure 1:
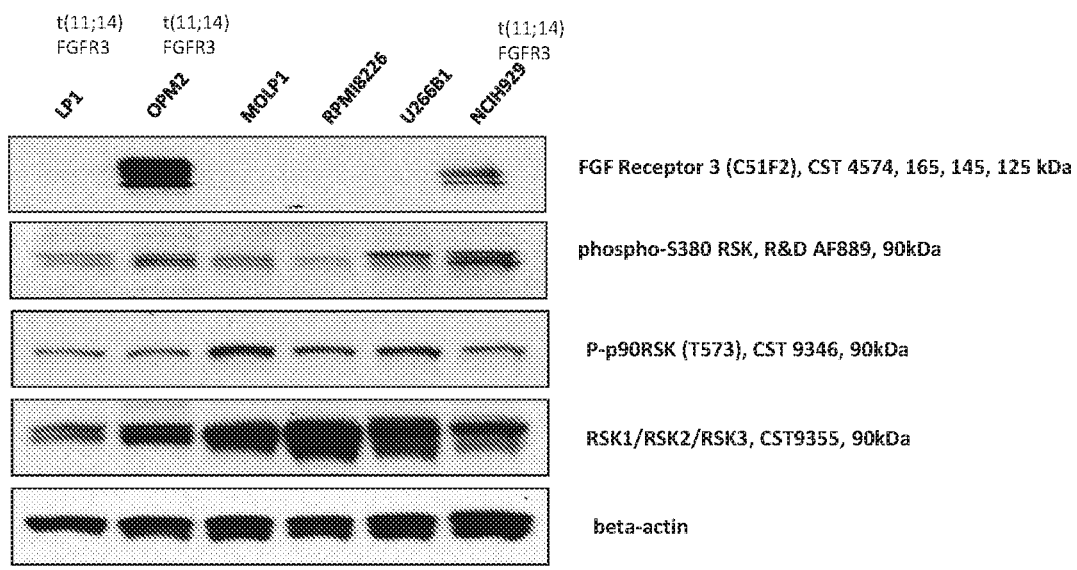
FIG. 1 presents gel pictures showing basal p90RSK expression in various multiple myeloma cell lines. The expression levels of phospho-p90RSK or RSK-S380 were not associated with FGFR3 expression.

It is to be understood that this disclosure is not limited to particular embodiments described, as such may, of course, vary. It is also to be understood that the terminology used herein is for the purpose of describing particular embodiments only, and is not intended to be limiting, since the scope of the present disclosure will be limited only by the appended claims.

1. Definitions

Unless defined otherwise, all technical and scientific terms used herein have the same meaning as commonly understood by one of ordinary skill in the art to which this disclosure belongs. As used herein the following terms have the following meanings.

It must be noted that as used herein and in the appended claims, the singular forms "a", "an", and "the" include plural referents unless the context clearly dictates otherwise. Thus, for example, reference to "an agent" includes a plurality of agents.

As used herein, the term "comprising" or "comprises" is intended to mean that the compositions and methods include the recited elements, but not excluding others. "Consisting essentially of" when used to define compositions and methods, shall mean excluding other elements of any essential significance to the combination for the stated purpose. Thus, a composition consisting essentially of the elements as defined herein would not exclude other materials or steps that do not materially affect the basic and novel characteristic(s) claimed. "Consisting of" shall mean excluding more than trace elements of other ingredients and substantial method steps. Embodiments defined by each of these transition terms are within the scope of this disclosure.

The term "about" when used before a numerical designation, e.g., temperature, time, amount, and concentration, including range, indicates approximations which may vary by (+) or (−) 10%, 5% or 1%.

As used herein, the term "treating and/or preventing" refers to preventing, curing, reversing, attenuating, alleviating, minimizing, suppressing or halting tumor growth, spreading, metastasis, or development.

As used herein, the term "patient" refers to a subject having a cancer or tumor, which can be benign or malignant. In certain embodiments, the patent is a human or an animal.

As used herein, the term "pharmaceutically acceptable" indicates that the indicated material does not have properties that would cause a reasonably prudent medical practitioner to avoid administration of the material to a patient, taking into consideration the disease or conditions to be treated and the respective route of administration. For example, it is commonly required that such a material be essentially sterile.

As used herein, the term "pharmaceutically acceptable carrier" refers to pharmaceutically acceptable materials, compositions or vehicles, such as a liquid or solid filler, diluent, excipient, solvent or encapsulating material, involved in carrying or transporting any supplement or composition, or component thereof, from one organ, or portion of the body, to another organ, or portion of the body, or to deliver an agent to the cancerous tissue or a tissue adjacent to the cancerous tissue.

As used herein, the term "formulated" or "formulation" refers to the process in which different chemical substances, including one or more pharmaceutically active ingredients, are combined to produce a dosage form. In certain embodiments, two or more pharmaceutically active ingredients can be co-formulated into a single dosage form or combined dosage unit, or formulated separately and subsequently combined into a combined dosage unit. A sustained release formulation is a formulation which is designed to slowly release a therapeutic agent in the body over an extended period of time, whereas an immediate release formulation is a formulation which is designed to quickly release a therapeutic agent in the body over a shortened period of time.

As used herein, the term "delivery" refers to approaches, formulations, technologies, and systems for transporting a pharmaceutical composition in the body as needed to safely achieve its desired therapeutic effect. In some embodiments, an effective amount of the composition is formulated for delivery into the blood stream of a patient.

As used herein, the term "solution" refers to solutions, suspensions, emulsions, drops, ointments, liquid wash, sprays, liposomes which are well known in the art. In some embodiments, the liquid solution contains an aqueous pH buffering agent which resists changes in pH when small quantities of acid or base are added.

2. Myeloma Treatments

As shown in the examples, cerdulatinib dose-dependently activated apoptosis and inhibited cell proliferation of various multiple myeloma (MM) cell lines and had potent cytotoxicity in other myeloma cancer cells including those of acute myeloid lymphoma (AML) and myeloproliferative diseases (MPD). Therefore, the experimental data presented here show that cerdulatinib is an efficacious anti-cancer agent for various myelomas and disorders.

Cerdulatinib is a small molecule, ATP-competitive, reversible inhibitor of both SYK and JAK family members. Cerdulatinib has a chemical name of 4-(cyclopropylamino)-2-(4-(4-(ethylsulfonyl)piperazin-1-yl)phenylamino)pyrimidine-5-carboxamide, and the chemical structure of formula I:

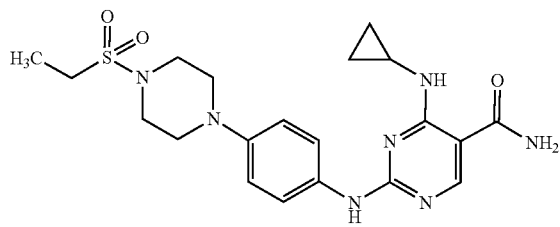

I

In accordance with one embodiment of the disclosure, provided is a method of treating a myelomas or a plasma cell disorder, such as multiple myeloma (MM), acute myeloid lymphoma (AML) and a myeloproliferative disease (MPD). In some aspects, the method comprises administering to a human patient in need thereof an effective amount of cerdulatinib, 4-(cyclopropylamino)-2-(4-(4-(ethylsulfonyl)piperazin-1-yl)phenylamino)pyrimidine-5-carboxamide, or a pharmaceutically acceptable salt thereof.

In some aspects, the method does not include administration of fludarabine (or the patient is not concurrently treated with fludarabine). Fludarabine is a purine analog that interferes with DNA synthesis. In some aspects, the method does not include administration of a purine analog (or the patient is not concurrently treated with a purine analog). In some aspects, the method does not include administration of an agent that interferes with DNA synthesis (or the patient is not concurrently treated with an agent that interferes with DNA synthesis).

The data show that cerdulatinib is efficacious in myeloma cells regardless of FGFR3 status. In one embodiment, therefore, cerdulatinib is administered to a patient that has an FGFR3 mutation, such as the t(11;24) or the t(4;14) translocation mutation (FGFR3 positive). In one embodiment, cerdulatinib is administered to a patient that has a wild-type FGFR3.

It is contemplated that cerdulatinib treatment is applicable to a myeloma patient that is at an advanced stage, or that is resistant (refractory) to other chemotherapeutic drugs, or a myeloma patient that has been prior-treated with one or more other chemotherapeutic drugs.

It is contemplated that cerdulatinib treatment is applicable to a myeloma patient that falls into any category, subcategory, or stage of the diseases, e.g., MM, AML or MPD, such as those described below.

Multiple Myeloma (MM)
Durie-Salmon Staging

In this system, there are three stages of myeloma: Stage I, Stage II, and Stage III. The stage depends on factors including:
  The amount of myeloma cells in the body
  The amount of damage the myeloma cells have caused to the bone
  Levels of M-protein in the blood or urine
  Blood calcium levels
  Albumin and hemoglobin levels Myeloma can also be further classified into Group A or Group B, based on damage to the kidneys. Group A indicates normal kidney function while Group B indicates abnormal kidney function. A person could be classified, for example, as Stage IIB.

International Staging System (ISS)

This staging system is based on the albumin level (more or less than 3.5 mg/dL) and B2-microglobulin level (<3.5; 3.5-5 or >5 mg/L). The higher the stage, the poorer the outcome. This staging system is based on outcomes of more than 10,000 cancer patients ?.

Types

There are different forms of myeloma-related conditions as detailed below. Some require treatment, some do not, but all will require regular check-ups to monitor whether the disease is progressing.

Monoclonal Gammopathy of Undetermined Significance (MGUS)

People who have MGUS harbor a small number of myeloma cells in the bone marrow but these cells do not form a tumor and symptoms of the myeloma are not present. This condition is usually discovered during a routine blood exam that shows unusual levels of protein in the blood.

MGUS is a pre-cancerous condition. Therefore, check-ups should occur every six months to monitor the condition and make sure that it does not develop into multiple myeloma, even though this only happens in a small amount of patients.

A diagnosis of MGUS should not be made without having performed chromosome analysis, gene array, MRI, and/or a PET/CT scan.

Asymptomatic (Smoldering/Indolent) Myeloma

Asymptomatic myeloma falls somewhere between MGUS and overt, symptomatic multiple myeloma. In this condition, a person has a greater number of myeloma cells than a person with MGUS. However, the disease does not cause any damage to the body and the typical myeloma symptoms are not present, though patients may exhibit anemia due to causes other than the myeloma.

Asymptomatic myeloma can be stable for many months or years, but it ultimately tends to progress. Treatment will likely be needed at some point. Patients will need to be monitored to see if the disease progresses and if symptoms become evident.

Symptomatic (Active) Myeloma

This type of myeloma represents overt cancer. A person with symptomatic myeloma has more myeloma cells than a person with asymptomatic myeloma or MGUS.

At this point, the disease is causing damage to the body, like bone damage, anemia, kidney problems, or hypercalcemia (high levels of calcium in the blood).

Acute Myeloid Leukemia (AML)

According to the widely used WHO criteria, the diagnosis of AML is established by demonstrating involvement of more than 20% of the blood and/or bone marrow by leukemic myeloblasts. The French-American-British (FAB) classification requires a blast percentage of at least 30% in bone marrow (BM) or peripheral blood (PB) for the diagnosis of AML. myeloproliferative syndromes, which are treated differently.

The WHO subtypes of AML include (1) acute myeloid leukemia with recurrent genetic abnormalities, which include:
- AML with translocations between chromosome 8 and 21-[t(8;21)(q22;q22);] RUNX1/RUNX1T1;
- AML with inversions in chromosome 16-[inv(16) (p13.1q22)] or internal translocations in it-[t(16;16) (p13.1;q22);] CBFB/MYH11; (ICD-O 9871/3);
- Acute promyelocytic leukemia with translocations between chromosome 15 and 17-[t(15;17)(q22;q12);] RARA/PML; (ICD-O 9866/3);
- AML with translocations between chromosome 9 and 11-[t(9;11)(p22;q23);] MLLT3/MLL;
- AML with translocations between chromosome 6 and 9-[t(6;9)(p23;q34);] DEK/NUP214;
- AML with inversions in chromosome 3-[inv(3) (q21q26.2)] or internal translocations in it-[t(3;3)(q21; q26.2);] RPN1/EVI1;
- Megakaryoblastic AML with translocations between chromosome 1 and 22-[t(1;22)(p13;q13);] RBM15/MKL1;
- AML with mutated NPM1; and
- AML with mutated CEBPA;

(2) acute myeloid leukemia with recurrent genetic abnormalities, which include:
- AML with complex karyotype Unbalanced abnormalities AML with deletions of chromosome 7-[del(7q);]
- AML with deletions of chromosome 5-[del(5q);]
- AML with unbalanced chromosomal aberrations in chromosome 17-[i(17q)/t(17p);]
- AML with deletions of chromosome 13-[del(13q);]
- AML with deletions of chromosome 11-[del(11q);]
- AML with unbalanced chromosomal aberrations in chromosome 12-[del(12p)/t(12p);]
- AML with deletions of chromosome 9-[del(9q);]
- AML with aberrations in chromosome X-[idic(X)(q13);]
- Balanced abnormalities AML with translocations between chromosome 11 and 16-[t(11;16)(q23;q13.3);], unrelated to previous chemotherapy or ionizing radiation;
- AML with translocations between chromosome 3 and 21-[t(3;21)(q26.2;q22.1);], unrelated to previous chemotherapy or ionizing radiation
- AML with translocations between chromosome 1 and 3-[t(1;3)(p36.3;q21.1);]
- AML with translocations between chromosome 2 and 11-[t(2;11)(p21;q23);], unrelated to previous chemotherapy or ionizing radiation
- AML with translocations between chromosome 5 and 12-[t(5;12)(q33;p12);]
- AML with translocations between chromosome 5 and 7-[t(5;7)(q33;q11.2);]
- AML with translocations between chromosome 5 and 17-[t(5;17)(q33;p13);]
- AML with translocations between chromosome 5 and 10-[t(5;10)(q33;q21);] and
- AML with translocations between chromosome 3 and 5-[t(3;5)(q25;q34);]

(3) therapy-related myeloid neoplasms, (4) myeloid sarcoma, (5) myeloid proliferations related to Down syndrome, (6) blastic plasmacytoid dendritic cell neoplasm, and (7) AML not otherwise categorized, such as:
- AML with minimal differentiation;
- AML without maturation;
- AML with maturation;
- Acute myelomonocytic leukemia;
- Acute monoblastic and monocytic leukemia;
- Acute erythroid leukemia;
- Acute megakaryoblastic leukemia;
- Acute basophilic leukemia; and
- Acute panmyelosis with myelofibrosis.

Myeloproliferative Diseases (MPD)

Myeloproliferative diseases include the following classes: (1) chronic myelogenous leukemia (CML); (2) essential thrombocythemia (ET); (3) polycythemia vera (PV); and (4) primary myelofibrosis (PMF). MPD can be a cellular phase or fibrotic phase.

3. Combination Treatments

In one embodiment, the treatment method can further include a chemotherapeutic agent useful for treating the cancer. In another embodiment, cerdulatinib is co-administered (simultaneously or sequentially) with a second agent. In one embodiment, the second agent is a chemotherapeutic agent. In one embodiment, the second agent can be selected from one of the classes detailed below.

Polyfunctional alkylating agents, exemplified by cyclophosphamide (cytoxan), mechlorethamine, melphalan (alkeran), chlorambucil (leukeran), thiopeta (thioplex), busulfan (myleran);

Alkylating drugs, exemplified by procarbazine (matulane), dacarbazine (dtic), altretamine (hexalen), clorambucil, cisplatin (platinol), carboplatin, ifosafamide, oxaliplatin;

Antimetabolites, exemplified by methotrexate (MTX), 6-thiopurines (mercaptopurine [6-mp], thioguanine [6-TG]), mercaptopurine (purinethol), thioguanine, fludarabine phosphate, cladribine: (leustatin), pentostatin, flurouracil (5-Fu), cytarabine (ara-C), azacitidine;

Plant alkaloids, terpenoids and topoisomerase inhibitors, exemplified by vinblastine (velban), vincristine (oncovin), vindesine, vinorelbine, podophyllotoxins (etoposide (VP-16) and teniposide (VM-26)), camptothecins (topotecan and irinotecan), taxanes such as paclitaxel (taxol) and docetaxel (taxotere);

Antibiotics, exemplified by doxorubicin (adriamycin, rubex, doxil), daunorubicin, idarubicin, dactinomycin (cosmegen), plicamycin (mithramycin), mitomycin: (mutamycin), bleomycin (blenoxane);

Hormonal agents, exemplified by estrogen and androgen inhibitors (tamoxifen and flutamide), gonadotropin-releasing hormone agonists (leuprolide and goserelin (Zoladex)), aromatase inhibitors (aminoglutethimide and anastrozole (arimidex));

Miscellaneous Anticancer Drugs, exemplified by amsacrine, asparaginase (El-spar), hydroxyurea, mitoxantrone (novantrone), mitotane (lysodren), retinoic acid derivatives, bone marrow growth factors (sargramostim and filgrastim), amifostine;

Agents disrupting folate metabolism, e.g., pemetrexed;

DNA hypomethylating agents, e.g., azacitidine, decitabine;

Poly(adenosine diphosphate [ADP]-ribose) polymerase (PARP) pathway inhibitors, such as iniparib, olaparib, veliparib;

PI3K/Akt/mTOR pathway inhibitors, e.g., everolimus;

Histone deacetylase (HDAC) inhibitors, e.g., vorinostat, entinostat (SNDX-275), mocetinostat (MGCD0103), panobinostat (LBH589), romidepsin, valproic acid;

Cyclin-dependent kinase (CDK) inhibitors, e.g., flavopiridol, olomoucine, roscovitine, kenpaullone, AG-024322

(Pfizer), fascaplysin, ryuvidine, purvalanol A, NU2058, BML-259, SU 9516, PD-0332991, P276-00;

Heat shock protein (HSP90) inhibitors, e.g., geldanamycin, tanespimycin, alvespimycin, radicicol, deguelin, BIIB021;

Murine double minute 2 (MDM2) inhibitors, e.g., cis-imidazoline, benzodiazepinedione, spiro-oxindoles, isoquinolinone, thiophene, 5-deazaflavin, tryptamine;

Anaplastic lymphoma kinase (ALK) inhibitors, e.g., aminopyridine, diaminopyrimidine, pyridoisoquinoline, pyrrolopyrazole, indolocarbazole, pyrrolopyrimidine, dianilinopyrimidine; or Poly [ADPribose] polymerase (PARP) inhibitors, illustrated by benzamide, phthalazinone, tricyclic indole, benzimidazole, indazole, pyrrolocarbazole, phthalazinone, or isoindolinone.

In some embodiments, the other chemotherapeutic agent is a p90RSK inhibitor, such as those described in Cohen et al., "A clickable inhibitor reveals context-dependent autoactivation of p90 RSK," Nat Chem Biol. 2007 March; 3(3): 156-160, and U.S. Pat. No. 7,605,241. In one aspect, the p90RSK inhibitor is one or more of dexamethasone, melphalan, doxorubicin, bortezomib, lenalidomide, prednisone, carmustine, etoposide, cisplatin, vincristine, cyclophosphamide, BI-D1870, and thalidomide.

4. Administration, Compositions and Dosing

Any effective regimen for administering cerdulatinib may be used. For example, the cerdulatinib may be administered as a single dose, oral, as an infusion, or as a multiple-dose daily regimen. The route of administration may also depend on the type of cancer. For example, for cancers such as lymphoma or leukemia, the administration may be systemic or oral, whereas a localized delivery may be used for treating a tumor. Further, a staggered regimen, for example, one to five days per week can be used as an alternative to daily treatment.

The amounts of various compounds to be administered can be determined by standard procedures taking into account factors such as the compound $IC_{50}$, the biological half-life of the compound, the age, size, and weight of the subject, and the indication being treated. The importance of these and other factors are well known to those of ordinary skill in the art. Generally, a dose will be between about 0.01 and 50 mg/kg, or 0.1 and 20 mg/kg of the subject being treated. Multiple doses may be used.

In certain embodiments, the therapeutically effective amount of cerdulatinib used in the methods, either alone or in one of the prescribed combinations, is at least about 10 mg per day. In one embodiment, the therapeutically effective amount of cerdulatinib is at least about 10, 20, 30, 40, or 50 mg per dosage. In one embodiment, the therapeutically effective amount of cerdulatinib is at least about 10, 20, 30, 40, 50, 60, 70, 80, 90 or 100 mg per day.

In one embodiment, the therapeutically effective amount of cerdulatinib is from about 10 mg to 150 mg, from about 25 mg to 120 mg, from about 30 to 80 mg, from about 40 to 50 mg, or at least 30 mg, 35 mg, 40 mg, 45 mg, 50 mg, 55 mg, 60 mg, or 65 mg per day. In one embodiment, the therapeutically effective amount of cerdulatinib is at least about 15 mg, 20 mg, 25 mg, 30 mg, or 35 mg and is administered twice daily.

In certain embodiments, the therapeutically effective amount of cerdulatinib is no more about 500, 400, 300, 200, 150, 120, or 100 mg per day. In one embodiment, the therapeutically effective amount of cerdulatinib is no more than about 300, 200, 150, 120, 100, 90, 80, 70, 60, 55 or 50 mg per dosage.

In certain embodiments, the therapeutically effective amount of cerdulatinib is no more than about 100 mg, 95 mg, 90 mg, 85 mg, 80 mg, or 75 mg per day. In certain embodiments, the therapeutically effective amount of cerdulatinib is no more than 45 mg, 40 mg, 35 mg, or 30 mg and is administered twice daily.

In one embodiment, the cerdulatinib, whether alone or in combination with another agent, is administered at from about 10 mg to 200 mg, from about 25 mg to 150 mg, from about 50 to 120 mg, or from about 80 to 100 mg a day.

In one embodiment, the therapeutically effective amount of cerdulatinib, whether alone or in combination with another agent, is 25 mg to 120 mg daily. In some embodiments, the effective amount of cerdulatinib is 25 mg to 50 mg twice daily. In certain embodiments, the cerdulatinib, whether alone or in combination with another agent, is administered once, twice, three times or four times a day.

In one embodiment, the cerdulatinib, whether alone or in combination with another agent, is administered from about 30 mg to about 80 mg once a day. In one embodiment, the cerdulatinib, whether alone or in combination with another agent, is administered from about 15 mg to about 40 mg twice a day.

In one embodiment, 45 mg of cerdulatinib, whether alone or in combination with another agent, is administered twice daily. In one embodiment, 35 mg of cerdulatinib, whether alone or in combination with another agent, is administered twice daily.

In some embodiments, the effective amount of cerdulatinib, or a pharmaceutically acceptable salt thereof, is about 40 mg to about 50 mg twice daily.

In some embodiments, the effective amount of cerdulatinib, or a pharmaceutically acceptable salt thereof, is about 30 mg to about 40 mg twice daily.

The dose of cerdulatinib administered can range from about 5 mg to about 150 mg daily. In some embodiments, cerdulatinib is administered at 45 mg. 50 mg, 55 mg, 60 mg, 65 mg or even more. Further, the half-life of cerdulatinib is enough to afford once-daily dosing. In some aspects, the effective amount of cerdulatinib is from about 25 mg to about 140 mg daily, from 25 mg to 120 mg daily, from 30 mg to 110 mg daily, from 40 mg to 100 mg daily, from 45 mg to 90 mg daily, from 50 mg to 80 mg daily. In some aspects, the effective dose is at least 20 mg. 30 mg, 35 mg, 40 mg, 45 mg, 50 mg, 55 mg, 60 mg, 65 mg, 70 mg, 75 mg, or 80 mg daily. In some aspects, the effective dose is not greater than 150 mg, 140 mg. 130 mg. 120 mg, 110 mg, 100 mg, or 90 mg daily. In some aspects, the daily dose is about 30 mg, 45 mg, 50 mg, 55 mg, 60 mg, 65 mg, 70 mg, 75 mg, 80 mg, 85 mg, 90 mg, 95 mg, 100 mg, 110 mg, 120 mg, 130 mg, 140 mg, or 150 mg.

In some aspects, cerdulatinib is administered once daily or twice daily. For once daily, the dose can be about 40 mg, 45 mg, 50 mg, 55 mg, 60 mg, 65 mg, or 70 mg. For twice daily, each dosing can be about 25 mg. 30 mg. 35 mg, 40 mg, 45 mg, 50 mg, 55 mg or 60 mg.

In one embodiment, the cerdulatinib is administered in a composition. The present disclosure provides compositions comprising a cerdulatinib and a pharmaceutically acceptable carrier. Pharmaceutically acceptable carriers are known to one having ordinary skill in the art may be used, including water or saline. As is known in the art, the components as well as their relative amounts are determined by the intended use and method of delivery. The compositions provided in accordance with the present disclosure are formulated as a solution for delivery into a patient for treating cancer. Diluent or carriers employed in the compositions can be selected so that they do not diminish the desired effects of the cerdulatinib. Examples of suitable compositions include aqueous solutions, for example, a solution in isotonic saline, 5% glucose. Other well-known pharmaceutically acceptable liquid carriers such as alcohols, glycols, esters and amides, may be employed. In certain embodiments, the composition further comprises one or more excipients, such as, but not limited to ionic strength modifying agents, solubility enhancing agents, sugars such as mannitol or sorbitol, pH buffering agent, surfactants, stabilizing polymer, preservatives, and/or co-solvents.

In certain embodiments, a polymer matrix or polymeric material is employed as a pharmaceutically acceptable carrier or support for the anti-adhesion composition. The polymeric material described herein may comprise natural or unnatural polymers, for example, such as sugars, peptides, protein, laminin, collagen, hyaluronic acid, ionic and non-ionic water soluble polymers; acrylic acid polymers; hydrophilic polymers such as polyethylene oxides, polyoxyethylene-polyoxypropylene copolymers, and polyvinylalcohol; cellulosic polymers and cellulosic polymer derivatives such as hydroxypropyl cellulose, hydroxyethyl cellulose, hydroxypropyl methylcellulose, hydroxypropyl methylcellulose phthalate, methyl cellulose, carboxymethyl cellulose, and etherified cellulose; poly(lactic acid), poly(glycolic acid), copolymers of lactic and glycolic acids, or other polymeric agents both natural and synthetic. In certain embodiments, the anti-adhesion compositions provided herein is formulated as films, gels, foams, or and other dosage forms.

Suitable ionic strength modifying agents include, for example, glycerin, propylene glycol, mannitol, glucose, dextrose, sorbitol, sodium chloride, potassium chloride, and other electrolytes.

In certain embodiments, the solubility of the cerdulatinib may need to be enhanced. In such cases, the solubility may be increased by the use of appropriate formulation techniques, such as the incorporation of solubility-enhancing compositions such as mannitol, ethanol, glycerin, polyethylene glycols, propylene glycol, poloxomers, and others known in the art.

Formulations contemplated by the present disclosure may also be for administration by injection include aqueous or oil suspensions, or emulsions, with sesame oil, corn oil, cottonseed oil, or peanut oil, as well as elixirs, mannitol, dextrose, or a sterile aqueous solution, and similar pharmaceutical vehicles. The cerdulatinib can be administered systemically or directly at (or near) a tumor site. In some embodiments, the administration is intra-arterial or intravenous. Suitable means for administration include needle (including microneedle) injectors, infusion techniques, and catheter-based delivery.

Aqueous solutions in saline are also conventionally used for injection, but less preferred in the context of the present disclosure. Ethanol, glycerol, propylene glycol, liquid polyethylene glycol, and the like (and suitable mixtures thereof), cyclodextrin derivatives, and vegetable oils may also be employed. The proper fluidity can be maintained, for example, by the use of a coating, such as lecithin, by the maintenance of the required particle size in the case of dispersion and by the use of surfactants. The prevention of the action of microorganisms can be brought about by various antibacterial and antifungal agents, for example, parabens, chlorobutanol, phenol, sorbic acid, thimerosal, and the like.

Sterile injectable solutions are prepared by incorporating the component in the required amount in the appropriate solvent with various other ingredients as enumerated above, as required, followed by filtered sterilization. Generally, dispersions are prepared by incorporating the various sterilized active ingredients into a sterile vehicle which contains the basic dispersion medium and the required other ingredients from those enumerated above. In the case of sterile powders for the preparation of sterile injectable solutions, the preferred methods of preparation are vacuum-drying and freeze-drying techniques which yield a powder of the active ingredient plus any additional desired ingredient from a previously sterile-filtered solution thereof.

In making pharmaceutical compositions that include cerdulatinib, the active ingredient is usually diluted by an excipient or carrier and/or enclosed within such a carrier that can be in the form of a capsule, sachet, paper or other container. When the excipient serves as a diluent, it can be a solid, semi-solid, or liquid material (as above), which acts as a vehicle, carrier or medium for the active ingredient. Thus, the compositions can be in the form of films, gels, patches, powders, lozenges, sachets, cachets, elixirs, suspensions, emulsions, solutions, syrups, aerosols (as a solid or in a liquid medium), ointments containing, for example, up to 10% by weight of the active compounds, soft and hard gelatin films, gels, patches, sterile injectable solutions, and sterile packaged powders.

In certain embodiments, the cerdulatinib described herein, or a composition comprising the same, is lyophilized prior to, during, or after, formulation. Accordingly, also provided herein is a lyophilized composition comprising a cerdulatinib or composition comprising the same as described herein.

Some examples of suitable excipients include lactose, dextrose, sucrose, sorbitol, mannitol, starches, gum acacia, calcium phosphate, alginates, tragacanth, gelatin, calcium silicate, microcrystalline cellulose, polyvinylpyrrolidone, cellulose, sterile water, syrup, and methyl cellulose. The formulations can additionally include: lubricating agents such as talc, magnesium stearate, and mineral oil; wetting agents; emulsifying and suspending agents; preserving agents such as methyl-and propylhydroxy-benzoates; sweetening agents; and flavoring agents.

EXAMPLES

Example 1. Expression and Inhibition of p90RSK in Multiple Myeloma Cell Lines

Six multiple myeloma cell lines were tested in this example for the expression level of p90RSK. The cell lines included LP1, OPM2, MOLP1, RPMI8226, U266B1, and NCIH929. Beta-actin was used as control, and the expression levels of FGF receptor 3 (FGFR3), phospho-S380 RSK. and RSK1/RSK2/RSK3 were also measured.

As shown in FIG. 1, p90RSK was positive in all cell lines. Further, the expression levels of p90RSK (as well as of RSK-S380) were not associated with that of FGFR3, which was only detected in two of the cell lines. As annotated in the figure, three cell lines (LP1, OMP2, and NCIH929) had t(11;14) FGFR3 activation mutation.

Figure 2:
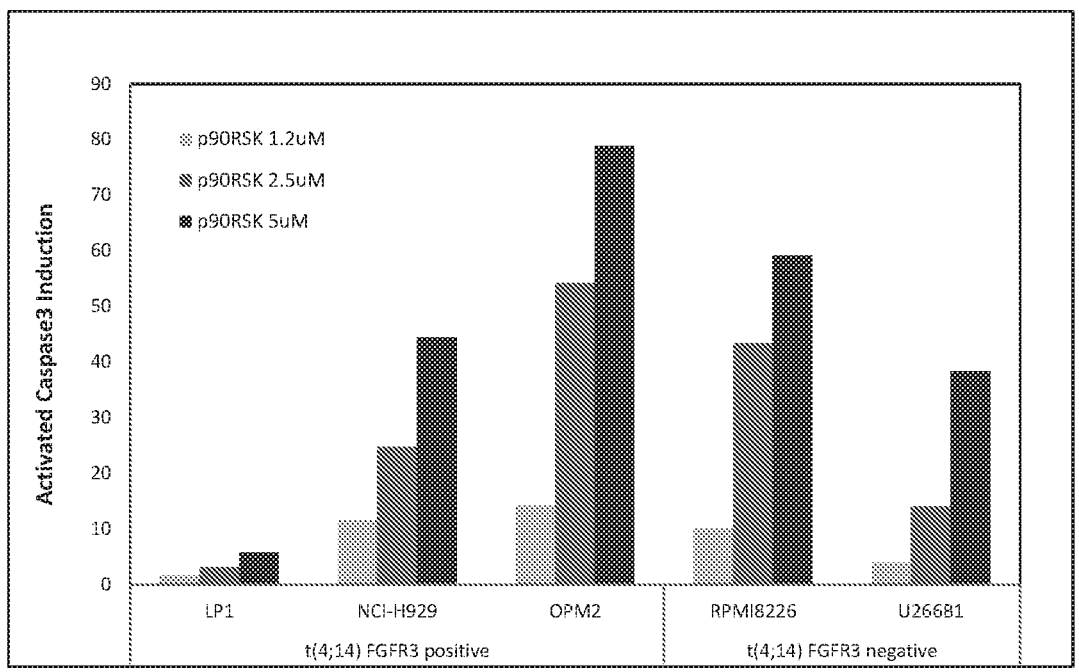
FIG. 2 is a chart showing that, in both FGFR3 positive and FGFR3 negative multiple myeloma cell lines, p90RSK inhibitor BI-D1870 dose-dependently activated caspase3 expression, an indication of induced apoptosis.

A p90RSK inhibitor, BI-D1870 (see, e.g., Sapkota et al., Biochem J. 2007, 401(Pt 1): 29-38), was added to the medium for each cell line at three difference concentrations. 1.2 µM, 2.5 µM, and 5 µM. As shown in FIG. 2, BI-D1870 dose-dependently activated the expression of Caspase3, an indicator of cell apoptosis. Further, the induction did not correlate with the FGFR3 status of the cell lines.

Figure 3:
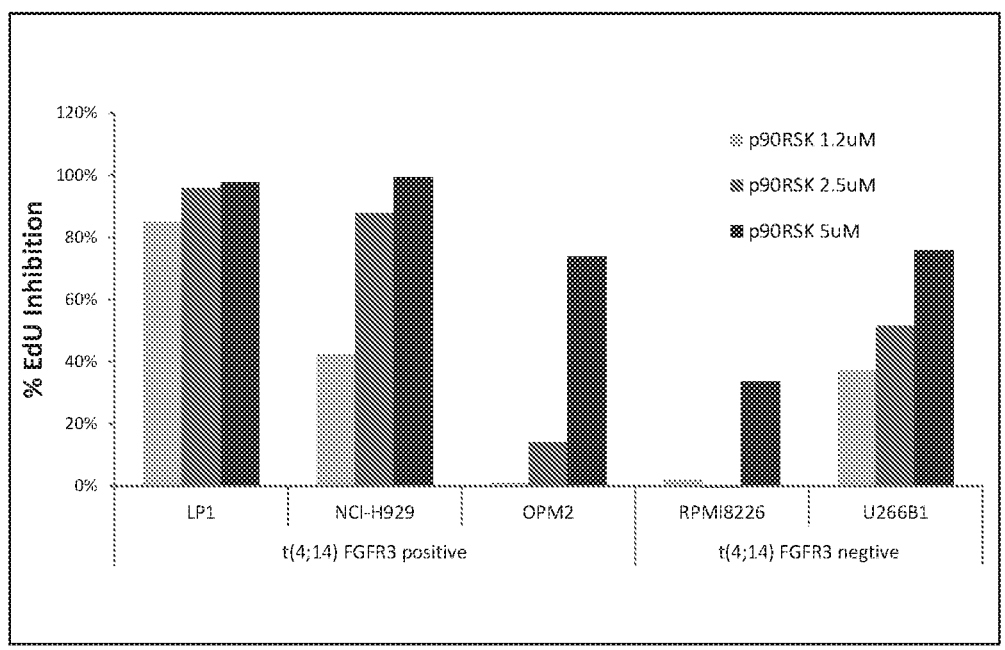
FIG. 3 is a chart showing that, in both FGFR3 positive and FGFR3 negative multiple myeloma cell lines, p90RSK inhibitor BI-D1870 dose-dependently inhibited cell proliferation (EdU as indicator).

In a similar experiment, BI-D1870 dose-dependently inhibited cell proliferation of the cell lines (FIG. 3), which inhibition also did not correlate with the FGFR3 status.

Figure 4:
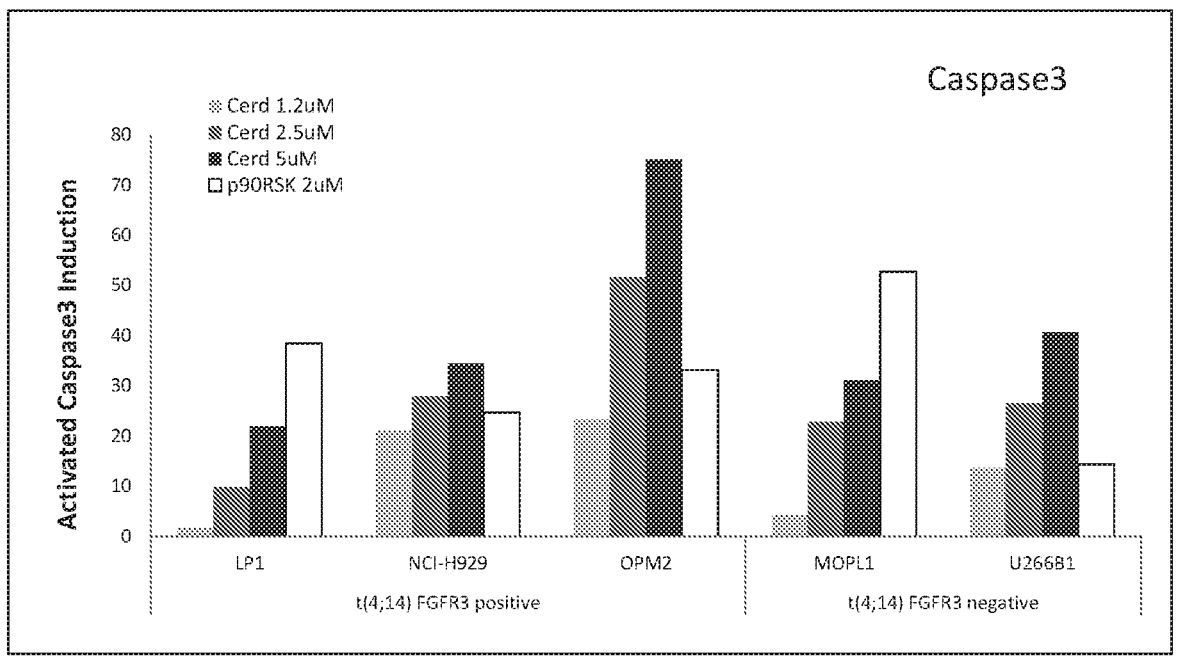
FIG. 4 is a chart showing that, like BI-D1870, cerdulatinib (Cerd) dose-dependently activated caspase3 expression, an indication of induced apoptosis, in both FGFR3 positive and FGFR3 negative multiple myeloma cell lines. Also, there was no relationship between FGFR3 expression and the sensitivity to cerdulatinib of the cell lines.
Figure 5:
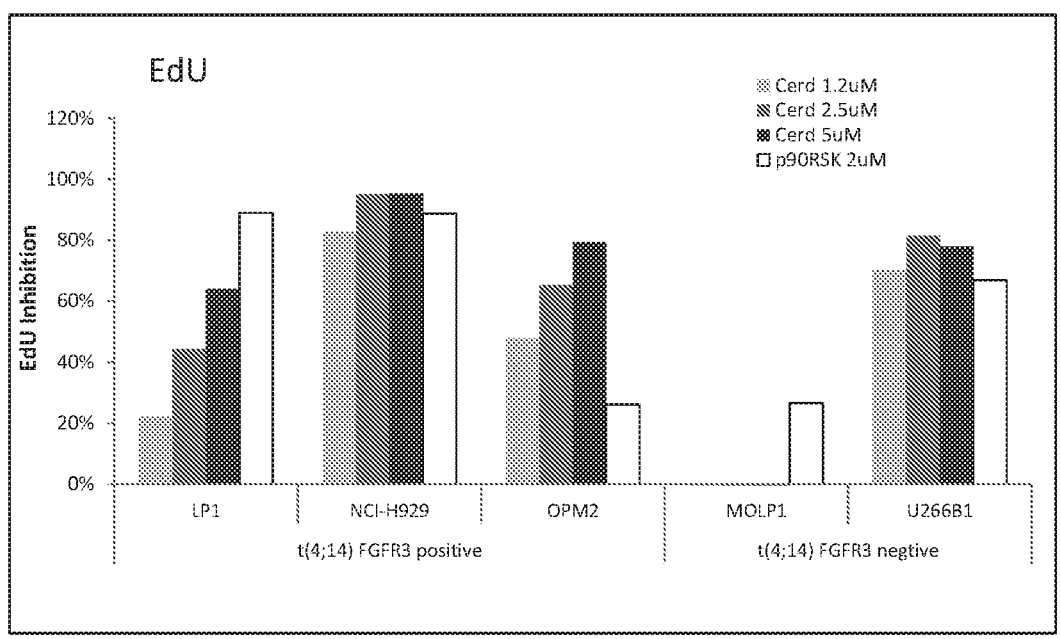
FIG. 5 is a chart showing that, like BI-D1870, cerdulatinib (Cerd) dose-dependently inhibited cell proliferation (EdU as indicator) in both FGFR3 positive and FGFR3 negative multiple myeloma cell lines. Also, there was no relationship between FGFR3 expression and the sensitivity to cerdulatinib of the cell lines.

Example 2. Cerdulatinib Activated Apoptosis and Inhibited Proliferation of Multiple Myeloma Cell Lines Cerdulatinib was tested with same cell lines as used in Example 1. As shown in FIGS. 4 and 5, like BI-D1870, cerdulatinib activated apoptosis and inhibited cell proliferation in these multiple myeloma cell lines. Also like BI-D1870, there was no relationship between the activity of cerdulatinib and the status of FGFR3.

This example suggests that cerdulatinib can treat multiple myeloma in an FGFR3-independently manner.

Example 3. Cerdulatinib is Potent in Killing Other Cancer Cells

Figure 6:
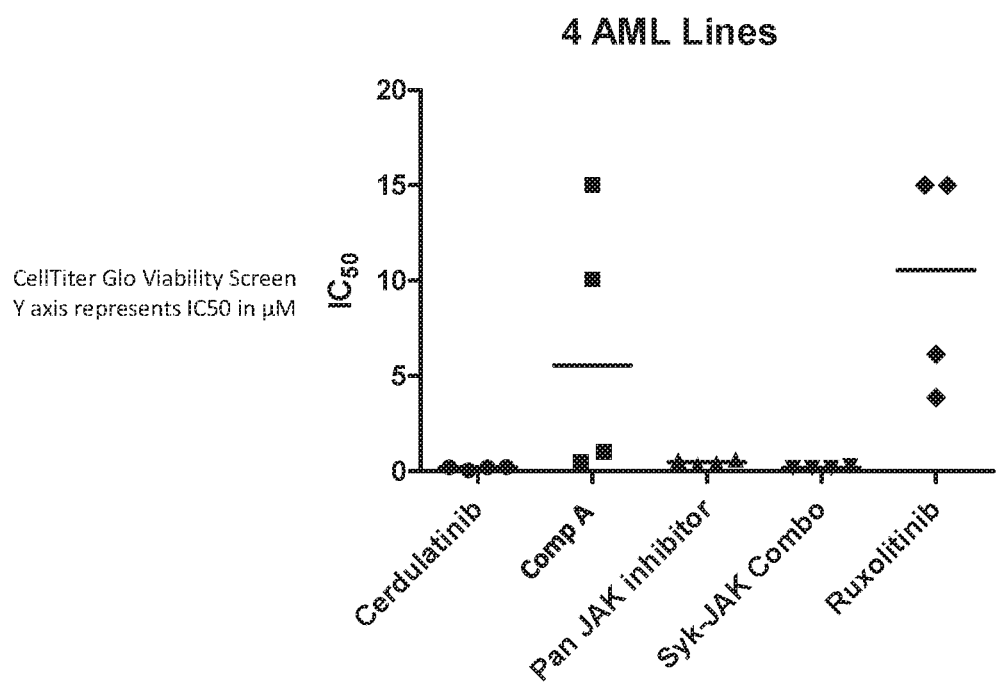
FIG. 6 is a chart showing that cerdulatinib was active in killing AML cells.

The cytotoxicity of cerdulatinib in AML (Acute Myeloid Leukemia) was tested in four different cell lines. As shown in FIG. 6, cerdulatinib was more active than Ruxolitinib, a JAK inhibitor, and Comp A (2-(((1R.2S)-2-aminocyclohexyl)amino)-4-(m-tolylamino)pyrimidine-5-carboxamide), a Syk inhibitor. This experiment, therefore, demonstrates cerdulatinib's ability in treating AML.

Figure 7:
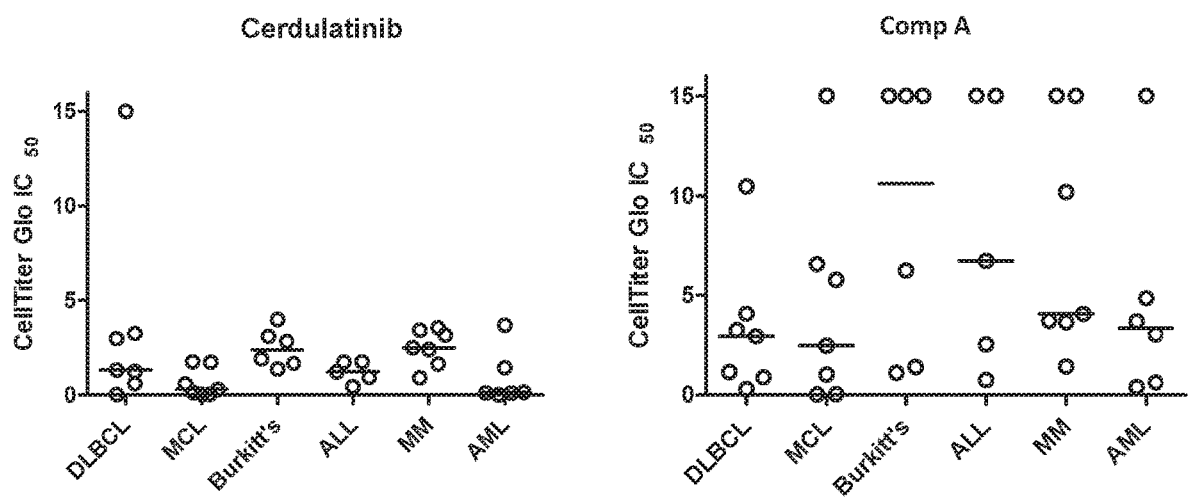
FIG. 7 compares the $IC_{50}$ of cerdulatinib to Comp A, a Syk inhibitor, across cancer types.

The cytotoxicity of cerdulatinib was also compared to Comp A in other types of cancer cells. As shown in FIG. 7, across DLBCL (Diffuse large B-cell lymphoma), MCL (Mantle Cell Lymphoma), Burkitt's lymphoma, ALL (Acute Lymphoblastic Leukemia), MM (Multiple Myeloma) and AML cells, cerdulatinib was more potent than Comp A, a potent Syk inhibitor.

Example 4. Drug Exposure and Dosing

Earlier studies had shown that the PK of cerdulatinib makes it suitable for once daily dosing with a half-life of 12-16 hours and a 2:1 peak-trough ratio. The present example, however, demonstrated that BID dosing could achieve even higher exposures, which was also tested clinically as described below.

Methods: This experiment was a 3+3 dose escalation study with 28-day cycles and doses studied ranging from 15 mg to 100 mg QD, and up to 45 mg BID. PK, PD, and safety were monitored. Clinical response was assessed by standard criteria. The level of inhibition of SYK and JAK was determined by multiple whole blood assays measuring signaling via BCR, IL2, IL4, IL6, and GM-CSF. Serum markers of tumor burden-CCL3, CCL4, and other markers of inflammation-B2M, CRP, were also measured.

Results: As of Jan. 7, 2016, 41 patients (pt) with CLL/SLL or B cell NHL were dosed. Median age was 67 years (range 23-85) and median prior therapies (tx) was 3 (range 1-8). Treatment emergent AEs of ≥ grade 3 observed deemed related to study drug were: neutropenia (n=2), anemia (n=1), and *pneumocystis* pneumonia (grade 5, n=1) at 30 mg; anemia, AST increase, hypotension, thrombocytopenia (n=1 for each), and fatigue (n=2) at 45 mg; anemia, neutropenia, abdominal pain, pneumonia, and fatigue (n=1 for each) at 50 mg, diarrhea and fatigue (n=1 for each) at 65 mg, nausea (n=1) at 100 mg, and pancreatitis (n=1) at 45 mg BID. The patient with grade 3 AST had tumor progression to the liver. The pancreatitis at 45 mg BID was considered at DLT and the cohort is expanding to approximately 6 patients.

In general. cerdulatinib was well tolerated. Ten total patients have remained on cerdulatinib for over 200 days, including two who have been on for a year or more. Once daily dosing of 40-100 mg resulted in 50 to 100% inhibition of SYK and JAK signaling at steady-state Cmin to Cmax, respectively, in peripheral blood of dosed patients. Significant inhibition of serum markers of inflammation was observed at these doses, and the extent of inhibition correlated with tumor response.

At the 45 mg BID dose level, complete inhibition of SYK and JAK at steady-state Cmin in peripheral blood assays was observed, consistent with an approximate doubling in exposure. Over the 40-100 mg dose range, the average steady state Cmin and Cmax concentrations plateaued at 0.70+0.20 and 1.38+0.23 µM, respectively. While PK is suitable for once daily dosing with a half-life of 12-16 hours and a 2:1 peak-trough ratio, the low pH solubility appeared to limit dissolution.

By switching to a 45 mg BID dose, steady-state Cmin was increased to approximately 1.5 µM, a concentration sufficient to induce apoptosis in pre-clinical tumor models using both primary cells and cell lines. Partial responses (n=4) were observed at 30 mg in a pt with del 17p CLL who had relapsed after 6 prior tx; at 45 mg a pt with CLL who had received 4 prior tx, and another pt with FL who had received 3 prior tx; and at 65 mg in a pt with a transformed DLBCL (MYC, BCL2, and BCL6 expression by IHC) who had relapsed approximately 1 year after 1 prior tx. Responses occurred after 2 cycles of tx. Thus far, the extent of tumor response significantly correlated with systemic exposure of drug, which has doubled in the 45 mg BID dose group relative to previous dose levels.

Unless otherwise defined, all technical and scientific terms used herein have the same meaning as commonly understood by one of ordinary skill in the art to which this invention belongs.

The inventions illustratively described herein may suitably be practiced in the absence of any element or elements, limitation or limitations, not specifically disclosed herein. Thus, for example, the terms "comprising", "including." "containing", etc. shall be read expansively and without limitation. Additionally, the terms and expressions employed herein have been used as terms of description and not of limitation, and there is no intention in the use of such terms and expressions of excluding any equivalents of the features shown and described or portions thereof. but it is recognized that various modifications are possible within the scope of the invention claimed.

Thus, it should be understood that although the present invention has been specifically disclosed by preferred embodiments and optional features, modification, improvement and variation of the inventions embodied therein herein disclosed may be resorted to by those skilled in the art, and that such modifications, improvements and variations are considered to be within the scope of this invention. The materials, methods, and examples provided here are representative of preferred embodiments, are exemplary, and are not intended as limitations on the scope of the invention.

The invention has been described broadly and generically herein. Each of the narrower species and subgeneric groupings falling within the generic disclosure also form part of the invention. This includes the generic description of the invention with a proviso or negative limitation removing any subject matter from the genus, regardless of whether or not the excised material is specifically recited herein.

In addition, where features or aspects of the invention are described in terms of Markush groups, those skilled in the art will recognize that the invention is also thereby described in terms of any individual member or subgroup of members of the Markush group.

All publications, patent applications, patents, and other references mentioned herein are expressly incorporated by reference in their entirety, to the same extent as if each were incorporated by reference individually. In case of conflict, the present specification, including definitions, will control.

It is to be understood that while the disclosure has been described in conjunction with the above embodiments, that the foregoing description and examples are intended to illustrate and not limit the scope of the disclosure. Other aspects, advantages and modifications within the scope of the disclosure will be apparent to those skilled in the art to which the disclosure pertains.

The invention claimed is:

1. A method of treating acute myeloid leukemia (AML) or a myeloproliferative disease (MPD) in a human patient in need thereof, comprising administering to the patient an effective amount of cerdulatinib or a pharmaceutically acceptable salt thereof, wherein the effective amount is from about 30 mg to about 80 mg daily and administration is twice daily, wherein the patient has an FGFR3 activation mutation.

2. The method of claim 1, wherein the patient is not being treated with fludarabine.

3. The method of claim 1, wherein the patient is not being treated with a purine analog.

4. The method of claim 1, wherein the patient is not being treated with an agent that interferes with DNA synthesis.

5. The method of claim 1, wherein the effective amount is about 15 mg, 20 mg, 25 mg, 30 mg, or 35 mg twice daily.

6. The method of claim 1, wherein the patient suffers from an advanced malignancy of AML or MPD.

7. The method of claim 1, wherein the patient has an albumin level lower than 3.5 mg/dL.

8. The method of claim 1, wherein the patient has a B2-microglobulin level from 3.5 to 5 mg/L or greater than 5 mg/L.

9. The method of claim 1, further comprising administering to the patient a second agent.

10. The method of claim 9, wherein the second agent is a P90RSK inhibitor.

11. The method of claim 9, wherein the second agent is selected from the group consisting of dexamethasone, melphalan, doxorubicin, bortezomib, lenalidomide, prednisone, carmustine, etoposide, cisplatin, vincristine, cyclophosphamide, BI-D1870, and thalidomide.

12. A method of treating acute myeloid leukemia (AML) or a myeloproliferative disease (MPD) in a human patient in need thereof, comprising administering to the patient an effective amount of cerdulatinib or a pharmaceutically acceptable salt thereof, wherein the effective amount is from about 30 mg to about 80 mg daily and administration is twice daily, wherein the patient has relapsed or not responded to a prior chemotherapy, wherein the patient has failed at least two prior therapies.

13. The method of claim 12, wherein the patient is not being treated with fludarabine.

14. The method of claim 12, wherein the patient is not being treated with a purine analog.

15. The method of claim 12, wherein the patient is not being treated with an agent that interferes with DNA synthesis.

16. The method of claim 12, wherein the effective amount is about 15 mg, 20 mg, 25 mg, 30 mg, or 35 mg twice daily.

17. The method of claim 12, wherein the patient suffers from an advanced malignancy of AML or MPD.

18. The method of claim 12, wherein the patient has an albumin level lower than 3.5 mg/dL.

19. The method of claim 12, wherein the patient has a B2-microglobulin level from 3.5 to 5 mg/L or greater than 5 mg/L.

20. The method of claim 12, further comprising administering to the patient a second agent.

21. The method of claim 20, wherein the second agent is a P90RSK inhibitor.

22. The method of claim 20, wherein the second agent is selected from the group consisting of dexamethasone, melphalan, doxorubicin, bortezomib, lenalidomide, prednisone, carmustine, etoposide, cisplatin, vincristine, cyclophosphamide, BI-D1870, and thalidomide.

* * * * *